(12) United States Patent
Biedermann et al.

(10) Patent No.: US 7,166,109 B2
(45) Date of Patent: Jan. 23, 2007

(54) BONE FIXATION DEVICE AND SCREW THEREFOR

(75) Inventors: Lutz Biedermann, VS-Villingen (DE); Peter Ostermann, Bocholt (DE); Jürgen Harms, Karlsruhe (DE)

(73) Assignee: Biedermann Motech GmbH (DE)

( * ) Notice: Subject to any disclaimer, the term of this patent is extended or adjusted under 35 U.S.C. 154(b) by 208 days.

(21) Appl. No.: 10/451,389

(22) PCT Filed: Jul. 26, 2002

(86) PCT No.: PCT/EP02/08358

§ 371 (c)(1),
(2), (4) Date: Jun. 19, 2003

(87) PCT Pub. No.: WO03/034930

PCT Pub. Date: May 1, 2003

(65) Prior Publication Data

US 2004/0039388 A1    Feb. 26, 2004

(30) Foreign Application Priority Data

Oct. 23, 2001    (EP) .................................. 01125150

(51) Int. Cl.
*A61B 17/56* (2006.01)
(52) U.S. Cl. ......................................................... 606/61
(58) Field of Classification Search ................. 606/60, 606/61, 72, 73, 69, 70, 71
See application file for complete search history.

(56) References Cited

U.S. PATENT DOCUMENTS

| | | | |
|---|---|---|---|
| 5,002,542 A | 3/1991 | Frigg | 606/61 |
| 5,024,213 A | 6/1991 | Asher et al. | 128/69 |
| 5,474,551 A * | 12/1995 | Finn et al. | 606/61 |
| 5,584,831 A | 12/1996 | McKay | 606/61 |
| 6,179,838 B1 | 1/2001 | Fiz | 606/61 |
| 6,187,005 B1 | 2/2001 | Brace et al. | 606/61 |
| 6,368,321 B1 * | 4/2002 | Jackson | 606/61 |
| 6,423,064 B1 | 7/2002 | Kluger | |

FOREIGN PATENT DOCUMENTS

| | | |
|---|---|---|
| DE | 199 44 120 A1 | 3/2001 |
| FR | 2 702 361 | 9/1994 |
| FR | 2 727 620 | 6/1996 |
| FR | 2 735 011 | 12/1996 |

* cited by examiner

Primary Examiner—Eduardo C. Robert
Assistant Examiner—Anuradha Ramana
(74) Attorney, Agent, or Firm—Christie, Parker & Hale, LLP

(57) ABSTRACT

A pelvis fixing device with a screw for the latter is provided. The screw comprises a screw element with a threaded shank and a head. Also provided is a holder which receives the head and which comprises a lower portion facing towards the shank side and an upper portion facing away from the shank side. The two portions encompass a rod. Also provided is a screw element for connecting the two portions and simultaneously fixing the rod. The pelvis fixing device comprises at least two such screws and at least one rod connecting them.

9 Claims, 4 Drawing Sheets

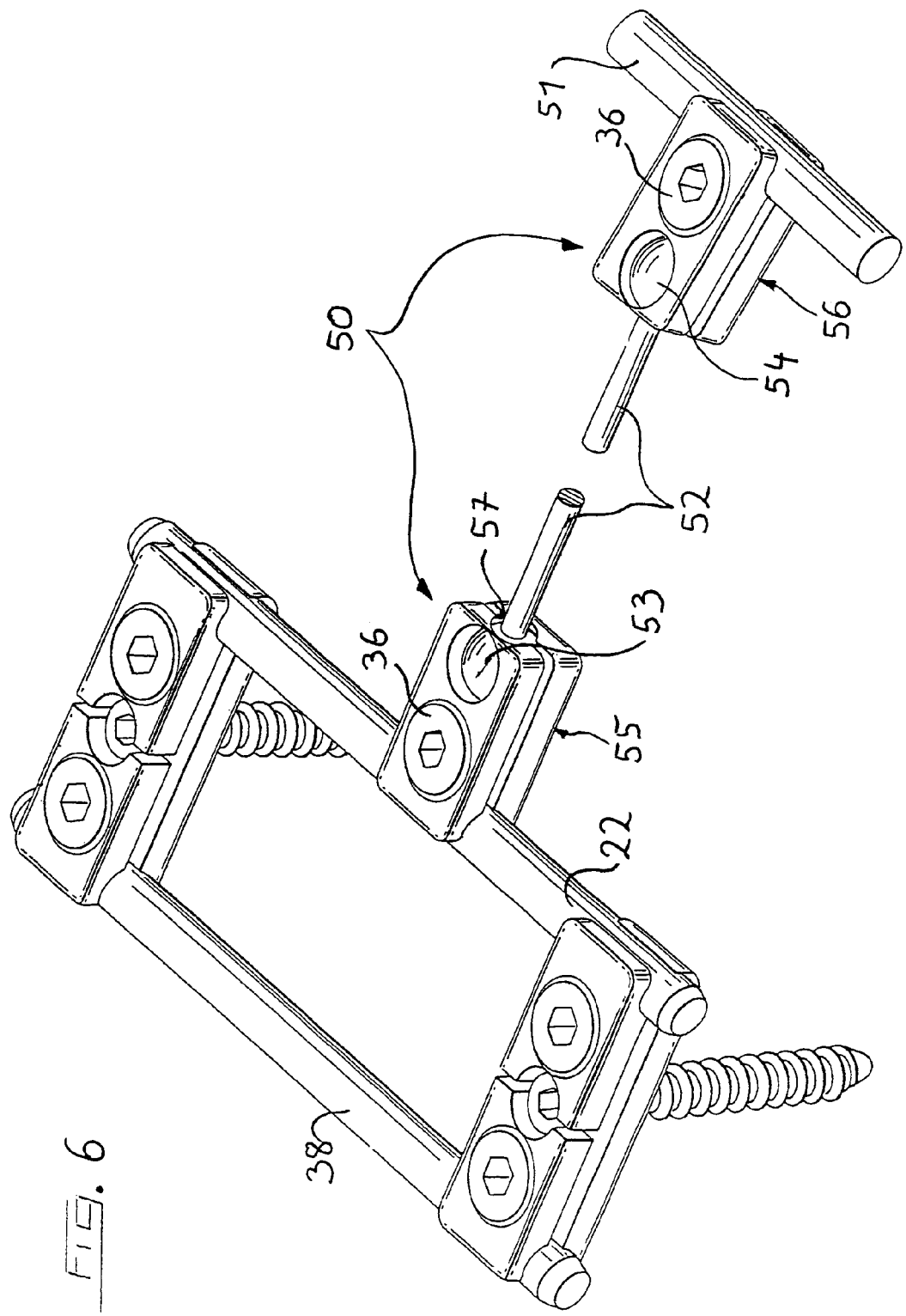

BONE FIXATION DEVICE AND SCREW THEREFOR

The invention concerns a device for fixing bones, in particular on the pelvis, or long bones, as well as screws for such a device.

BACKGROUND

For fixing bones, in particular on the pelvis, or long bones in case of a fracture, plates and screws are used in a known manner. These are constructed so as to be to some extent adaptable to the curvature of the bone or pelvis portion to be fixed. The plate shape itself and the position of the screws therefor can be varied only to a minor extent.

From U.S. Pat. No. 5,002,542 is known a clamp for a bone screw, comprising two sections for receiving the head of the bone screw, a hook which receives a rod, and a clamping means which holds the two sections together so that they clamp fast the head of the bone screw and the rod guided by the hook. Due to the large number of different component parts, however, this clamp is very complicated to handle and elaborate to make.

U.S. Pat. No. 5,584,831 shows a bone fixing device with a bone screw and a clamp. The clamp consists of two portions which comprise ball segment-shaped recesses on one side for receiving the ball-shaped head of the bone screw and cylinder segment-shaped recesses on the other side for receiving a rod. The two portions are connected to each other by a screw so as to clamp fast the head of the bone screw on the one hand and the rod on the other hand. This fixing device too is complicated to handle and elaborate to make.

SUMMARY

It is the object of the invention to provide a fixing device and screws, with which repositioning and fixing, e.g. of a pelvis or of long bones, can be substantially improved, and in particular to provide a fixing device of low height. Further, the invention is to provide a fixing device which is as cheap as possible to produce and as easy as possible to handle. Further, the invention is to provide a fixing device in which the holder can be inserted together with the screw. Further, the invention is to provide a fixing device which is capable of fixing more than one rod.

A fixing device according to the present invention comprises at least one screw with a screw element and a holder which fixes the screw element and a rod and which comprises an upper portion and a lower portion. The screw element comprises a threaded shank portion with thread and a ball-shaped bead. The upper portion and lower portion of the holder comprise ball segment-shaped recesses on one side for receiving the ball-shaped head of the bone screw and cylinder segment-shaped recesses on the other side for receiving a rod. They are connected to each other by a screw cooperating with a thread formed between the ball segment-shaped and the cylinder segment-shaped recesses, so that the ball-shaped head of the screw and the rod are fixed simultaneously.

Preferably, the upper portion and lower portion are designed as flat, plate-shaped portions of identical construction and arranged symmetrically to a plane defined by the center line of the rod and the center of the ball-shaped head of the screw. As a result, a low height can be obtained. Moreover, as a result the number of parts to be provided is reduced, so that the fixing device is cheaper to make and easier to handle.

With an identical construction of upper portion and lower portion, a recess for passage of a tool for turning the screw element in the upper portion corresponds to the recess for passage of the threaded shank portion in the lower portion. As a result, the screw with preassembled holder can be screwed into the bone, which simplifies handling.

Preferably, the upper portion and lower portion of the holder are designed in such a way that in each case at the center is formed a ball segment-shaped recess for receiving the ball-shaped head, on either side is formed a thread for joining upper portion and lower portion, and at either end is formed a cylinder segment-shaped recess for receiving a rod each. In this way it is possible to connect more than one rod to a screw.

BRIEF DESCRIPTION OF THE DRAWINGS

Further characteristics and advantages of the invention are apparent from the description of practical examples with the aid of the figures. The figures show:

FIG. 6 a perspective view of a fifth embodiment.

DETAILED DESCRIPTION

Figure 1:
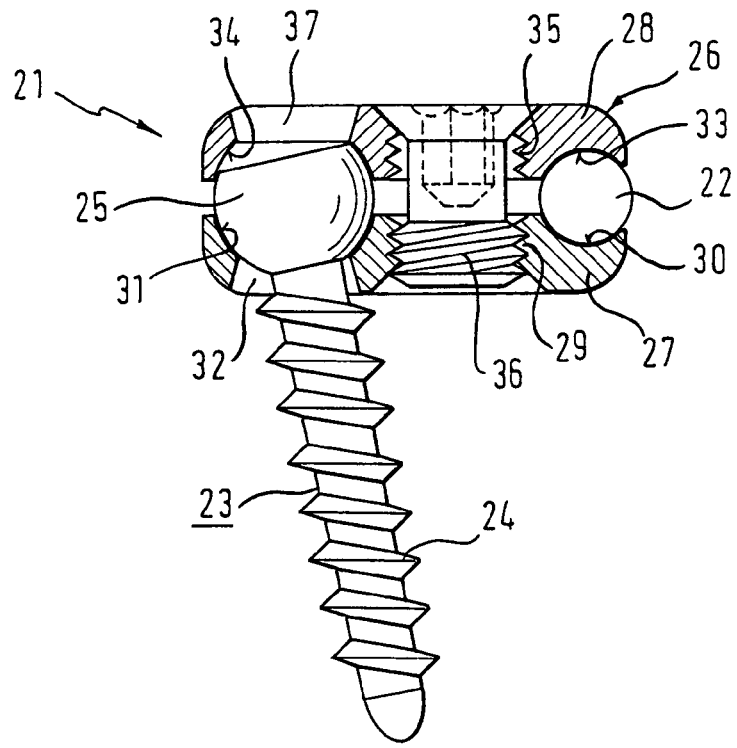
FIG. 1 a sectional side view of a first embodiment.

First, with reference to FIG. 1 a first embodiment of the present invention is described. As shown in FIG. 1 in a sectional side view, a bone screw 21 comprises a screw element 23 which comprises a threaded shank portion 24 and a spherical head 25, and a holder 26 which comprises a lower portion 27 and an upper portion 28.

The lower portion 27 and upper portion 28 are identically constructed and arranged symmetrically to a plane defined by the center line of the rod and the center of the ball-shaped head of the screw.

The lower portion 27 and upper portion 28 each comprise a central bore which is provided with an internal thread 29, 35 and comprises a countersink bore on the surface facing away from the other portion 27, 28. On one side of the central thread 29, 35 at a distance from the latter is provided a recess 30, 33 which is cylinder segment-shaped towards the other portion 27, 28. On the side of the central thread 29, 35 opposite this recess, the lower portion 27 and the upper portion 28 each comprise a ball segment-shaped recess 31, 34 on the side facing towards the other portion 27, 28. On the surface facing away from the other portion 27, 28, a cone-shaped recess 32, 37 which preferably increases outwardly adjoins coaxially with the recess 31, 34.

Further, a screw 36 is provided which can be introduced through the internal thread 35 of the upper portion and screwed into the internal thread 29 of the lower portion in the manner shown in FIG. 1. The screw has, in its portion which is passed through the upper portion 28, a diameter which is smaller than the inside diameter of the internal thread 35 of the upper portion and comprises, in its portion which is passed through the lower portion 27, an external thread cooperating with the internal thread 29 of the lower portion.

As can best be seen from FIG. 1, the two recesses 30 and 33 have the same radius which corresponds to the radius of a rod 22 to be received. Further, the two recesses 31 and 34 have the same radius which corresponds to the radius of the head 25. The recesses are in each case arranged round the common center point and defined in such a way that upper portion 28 and lower portion 27 are parallel to each other and at a distance from each other in the position shown in FIG. 1, in which rod and head are received.

During operation, the lower portion 27 and upper portion 28 are moved far enough away from each other by undoing the screw 36 and are then rotated relative to each other through 900. Then, first the screw 23 can be introduced through the preferably cone-shaped recess 32 of the lower portion 27 and screwed into a part to be fixed by means of a suitable tool. The head for this purpose comprises a corresponding recess for engagement with a screwdriver. Next the rod 22 is received. Then the upper portion 28 is rotated through 900 back into the position shown in FIG. 1, and then connection is effected by tightening the screw 36 in the fixed position shown in FIG. 1, in which both the screw and the rod are held tight by the head and so joined together. The preferably conical shape of the recess 32 of the lower portion 27 makes it possible to join screw 23 and holder 26 together so that they can be oriented multiaxially. A screwdriver can be introduced through the recess 37 of the upper portion, so that the screw 23 can be operated even when it is already joined to the holder 26.

A fixing device formed with such screws includes at least two such screws 21 and a rod 22 to be connected thereto, so that two parts to be joined together or fixed are held together in a desired position by means of the screws screwed in in this way and the rod.

Figure 2:
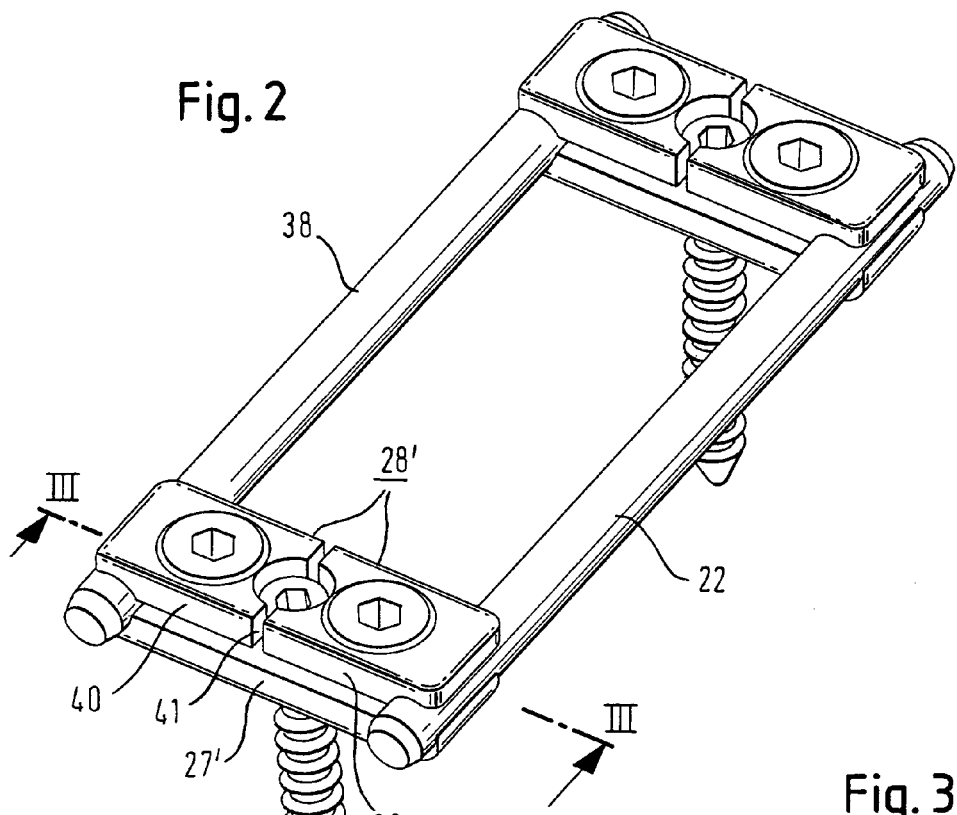
FIG. 2 a perspective view of a second embodiment.
Figure 3:
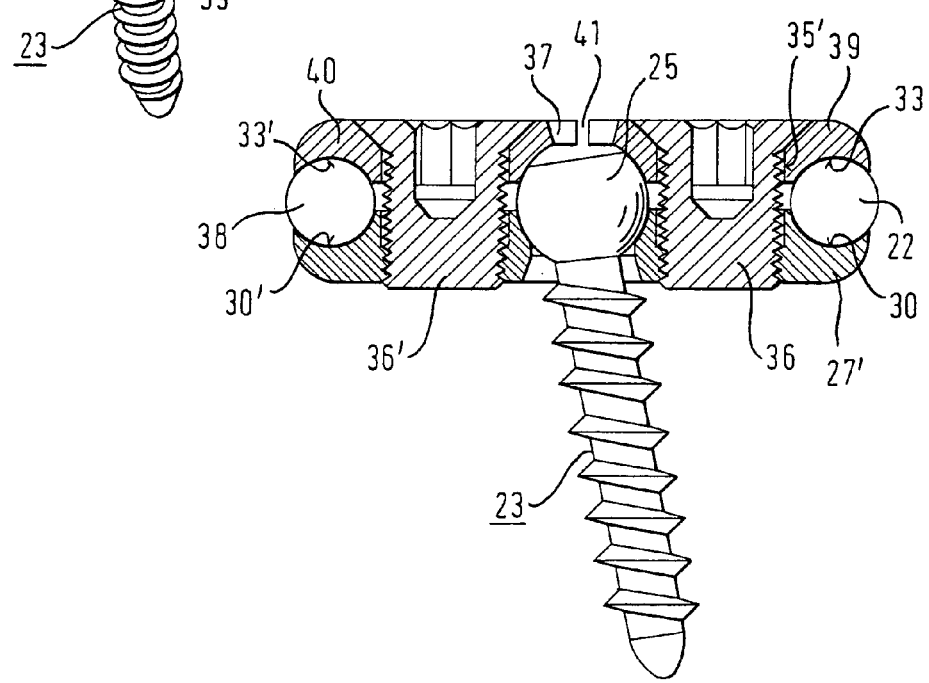
FIG. 3 a sectional side view along line III—III in FIG. 2.

To fix several bone portions relative to each other, to increase the stability it may be desirable to join the bone screw to more than one rod. In FIGS. 2 and 3 is shown a second embodiment of the present invention which is capable of joining two rods to the screw 23.

For this purpose the holder consisting of lower portion 27' and upper portion 28' is extended to one side opposite the first rod 22, for receiving a second rod 38. This extension can be designed in such a way that lower portion 27' and upper portion 28' are constructed inversely symmetrically to a plane which extends perpendicularly to the plane between upper portion and lower portion and parallel to the longitudinal axis of the rod 22 and passes through the center of the ball segment-shaped recesses 31, 34, so that on the side opposite the support for the rod 22 an identical support is provided for a second rod 38. For clamping, like the screw 36 between the head 25 and the rod 22, a corresponding screw between head 25 and rod 38 is designed as a screw 36'.

Lower portion 27' and upper portion 28' are not identically constructed in this embodiment. The lower portion 27 comprises on either side of the ball-shaped recess 31 a bore which is provided with an internal thread 29. The upper portion 28' comprises, coaxially with the internal thread 29 of the lower portion, a bore 35' which comprises a countersink bore on the surface facing away from the lower portion. The diameter of the bore 35' is selected such that a screw cooperating with the internal thread 29 can be passed through the bore.

As can be seen from FIGS. 2 and 3, in this embodiment the upper portion 28' is constructed in such a way that the first half 39 cooperating with the head 25 and the first rod 22, and the second half 40 cooperating with the head 25 and the second rod 38, are separated from each other by a slot 41 which extends transversely to a line which is defined by the centers of the screws 36, 36'.

The other characteristics correspond to those of the first embodiment and are not repeated at this point.

With this embodiment, two rods 22 and 38 can be held simultaneously, achieving substantially greater stabilization of the support for corresponding applications.

Figure 4:
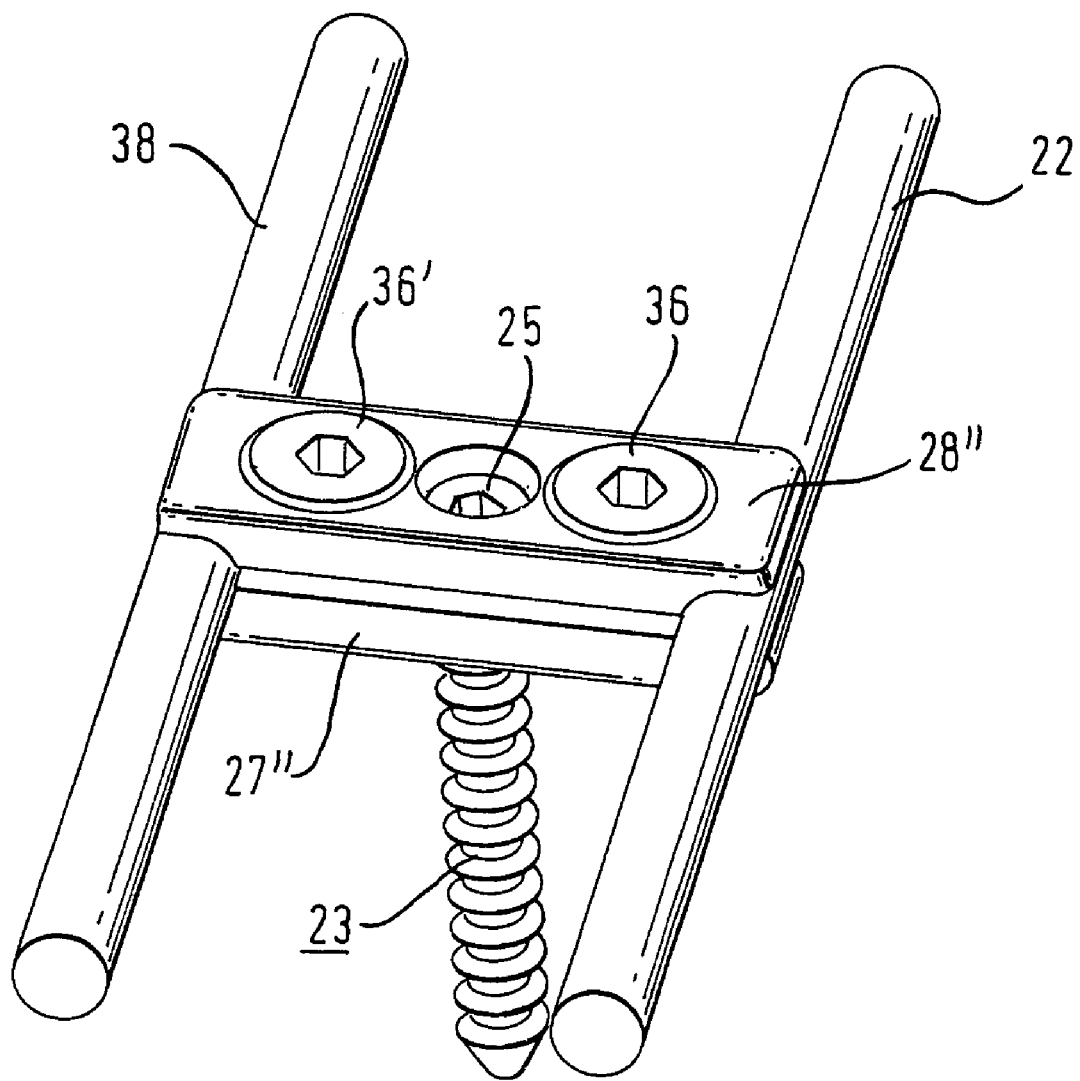
FIG. 4 a perspective view of a third embodiment.

A third embodiment shown in FIG. 4 differs from the second embodiment shown in FIGS. 2 and 3 only in that the upper portion 28' is not slotted.

Figure 5:
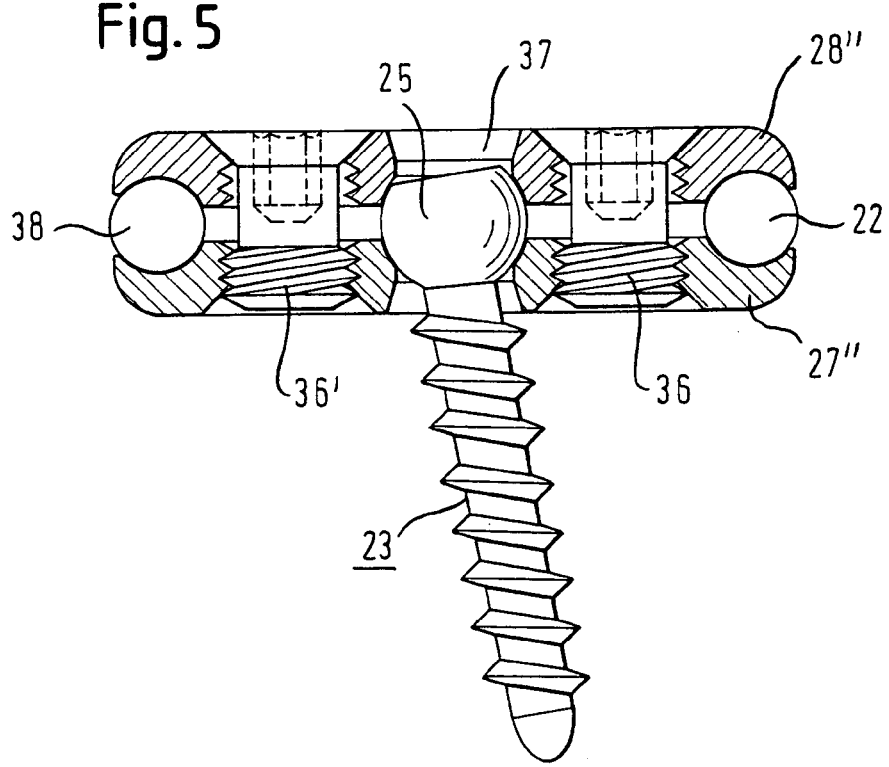
FIG. 5 a sectional side view along line III—III in FIG. 2 for a fourth embodiment.

In a fourth embodiment shown in FIG. 5, in the design for holding two rods too the upper portion and lower portion are constructed identically and arranged symmetrically to a plane defined by the center line of the rod 22 and the center of the ball-shaped head 25 of the screw.

As in the second embodiment, the lower portion 27" and upper portion 28" are constructed symmetrically in themselves, with the ball-shaped recess 31, 34 at the center. As in the first embodiment, both the lower portion 27" and upper portion 28" comprise on either side of the ball-shaped recess a bore which is provided with an internal thread 29, 35, and on the surface facing away from the other portion 27", 28" a countersink bore. The two screws 36, 36' have in their portion which is passed through the upper portion 28' a diameter which is smaller than the inside diameter of the internal thread 35 of the upper portion, and comprise in their portion which is passed through the lower portion 27 an external thread cooperating with the internal thread 29 of the lower portion.

The other characteristics correspond to those of the second embodiment and are not repeated at this point.

A fifth embodiment shown in FIG. 6 fully corresponds to one of the embodiments shown in FIGS. 2 to 5 with respect to the two rods 22, 38 and the holder connecting them. FIG. 6 shows in addition a device 50 for connecting a further rod 51 with the fixing device. The device 50 comprises a rod 52 designed as a shank, which is shown in broken form and comprises a ball 53, 54 at each of its two mutually opposed ends, and at each of its two ends a holder 55, 56, which are constructed identically in the embodiment shown. The latter correspond in construction to the holder 26 shown in FIG. 1, with the exception that in addition to the preferably conical recesses 32 and 34 there is provided a cone-shaped recess 57 which also preferably increases outwardly and whose center axis passes through the center of the bearing which is formed for the head 53, 54 and which corresponds to the bearing in FIG. 1 which receives the head 25, and in the embodiment shown lies in the plane between upper portion and lower portion and passes not only through the center of the ball 53, 54, but also through the center axis of the screw 36.

The dimensions between the ball 53 or 54 and the bearing are such that, if the screw 36 is loosened slightly, on the one hand sliding on the rod 22 or 51 is possible, on the other hand a pivot movement of the shank 52 through a cone is possible about the longitudinal axis of the preferably cone-shaped opening 57, so that non-parallel rods 22, 51 of this device can be connected as well. After connection, the screw 36 is tightened, with the result that the holder encompasses both the rods 22 or 51 and the ball heads 53 or 54 tightly.

In the embodiment shown in FIG. 6, the spherical recess 34 (FIG. 1) opens towards the upper side of the upper portion 28. But it is equally possible to form the upper portion and lower portion without the recesses 32, 37, so that the spherical recesses 31, 34 are closed towards the outer side.

In FIG. 6 the connecting device 50 is shown in connection with one of the embodiments shown in FIGS. 2 to 5 with two rods 22, 38. But the connecting device 50 can just as well be used together with the embodiment shown in FIG. 1 with a single rod 22.

Compared with the state of the art mentioned hereinbefore, the device according to the invention has the advantages that it needs fewer components and is therefore cheaper to make and easier to handle. As the rod and the screw are fixed simultaneously, there is easier adjustment and so in general easier handling. Further, there is the advantage of an extremely low height. The screw can be screwed with the preassembled holder into the bone, which further simplifies handling. Furthermore it is possible to connect more than one rod to a screw. The device according to the invention can also be used to connect rods to each other.

The invention claimed is:

1. A fixing device for fixing bones, the fixing device comprising:
    a first screw element having a threaded shank and a ball segment-shaped head;
    a holder for encompassing a rod, and for receiving the ball segment-shaped head of the first screw element, the holder comprising a lower portion and an upper portion; and
    a second screw element for connecting together the upper and lower portions and simultaneously fixing the first screw element and the rod in the holder;
    wherein each of the upper portion and the lower portion have a first threaded bore hole, the first threaded bore holes of the upper portion and the lower portion aligned to simultaneously receive the second screw element for connecting the two portions;
    wherein each of the upper portion and the lower portion have, on one side of the first threaded bore hole, a cylinder segment-shaped recess for receiving the rod and, on a side of the first threaded bore hole opposite the cylinder segment-shaped recess, a through hole comprising a ball segment-shaped portion for receiving the ball head and for passage of the threaded shank or a tool for turning the screw;
    wherein the upper and lower portions have identical structure and are arranged inversely symmetrically to each other to form the holder.

2. The fixing devices according to claim 1 further comprising a second fixing device connected to the fixing device.

3. The fixing device according to claim 1, wherein the upper portion and the lower portion include a second threaded bore hole for cooperation with a second screw element for connecting the upper and lower portions, and on one side of the second threaded bore hole a second cylinder segment-shaped recess for receiving a second rod.

4. The fixing device according to claim 3, wherein the screw is arranged between the first threaded bore hole and the second threaded bore hole.

5. A fixing device for fixing bones, the fixing device comprising:
    a first screw element comprising a threaded shank and a ball segment-shaped head;
    a holder for encompassing a rod, and for receiving the ball-segment shaped head of the first screw element, the holder comprising a lower portion and an upper portion; and
    a second screw element for connecting together the upper and lower portions and simultaneously fixing the first screw element and the rod in the holder;
    wherein each of the upper portion and the lower portion include a first threaded bore hole, the first threaded bore holes of the upper portion and the lower portion aligned to simultaneously receive the second screw element for connecting the upper and lower portions; wherein each of the upper portion and the lower portion have, on one side of the threaded bore hole, a cylinder segment-shaped recess for receiving the rod and, on a side of the threaded bore hole opposite the cylinder segment-shaped recess, a through hole comprising a ball segment-shaped portion for receiving the ball segment-shaped head and for passage of the threaded shank or a tool for turning the screw;
    wherein the upper and lower portions being arranged inversely to each other to form the holder.

6. The fixing device according to claim 5, wherein the upper portion has a slot dividing the upper portion into a first half and a second half which are separated by the slot.

7. The fixing device according to claim 6, wherein the slot communicates with the through hole.

8. The fixing device according to claim 5, wherein the upper portion and the lower portion include a third threaded bore hole for cooperation with a second screw element for connecting the upper and lower portions, and on one side of the second threaded bore hole a second cylinder segment-shaped recess for receiving a second rod.

9. The fixing device according to claim 8, wherein the screw is arranged between the first threaded bore hole and the second threaded bore hole.

* * * * *

UNITED STATES PATENT AND TRADEMARK OFFICE
CERTIFICATE OF CORRECTION

PATENT NO. : 7,166,109 B2  Page 1 of 1
APPLICATION NO. : 10/451389
DATED : January 23, 2007
INVENTOR(S) : Lutz Biedermann et al.

It is certified that error appears in the above-identified patent and that said Letters Patent is hereby corrected as shown below:

| | |
|---|---|
| Column 3, line 9 | Delete "900", Insert --90°-- |
| Column 3, line 15 | Delete "900", Insert --90°-- |
| Column 5, line 44, Claim 3 | Delete "second", Insert --third-- |
| Column 6, line 21, Claim 5 | Before "threaded bore", Insert --first-- |
| Column 6, line 23, Claim 5 | Before "threaded bore", Insert --first-- |

Signed and Sealed this

Twelfth Day of August, 2008

JON W. DUDAS
*Director of the United States Patent and Trademark Office*

UNITED STATES PATENT AND TRADEMARK OFFICE
CERTIFICATE OF CORRECTION

Page 1 of 1

PATENT NO. : 7,166,109 B2
APPLICATION NO. : 10/451389
DATED : January 23, 2007
INVENTOR(S) : Lutz Biedermann et al.

It is certified that error appears in the above-identified patent and that said Letters Patent is hereby corrected as shown below:

In the Specification

Column 3, line 9    Delete "900",
                    Insert --90°--

Column 3, line 15   Delete "900",
                    Insert --90°--

In the Claims

Column 5, Claim 3, line 45    Delete "second screw"
                              Insert --third screw--

Column 6, Claim 5, line 22    Before "threaded bore",
                              Insert --first--

Column 6, Claim 5, line 24    Before "threaded bore",
                              Insert --first--

Column 6, Claim 8, lines 37 and 38    Delete "a third threaded bore hole for
                                      cooperation with a second screw element"

Insert --a second threaded bore hole for cooperation with a
                                      third screw element--

This certificate supersedes the Certificate of Correction issued August 12, 2008.

Signed and Sealed this
Sixth Day of March, 2012

David J. Kappos
*Director of the United States Patent and Trademark Office*